(12) United States Patent
Murphy-Aniceto et al.

(10) Patent No.: US 8,376,750 B1
(45) Date of Patent: *Feb. 19, 2013

(54) ONLINE GAME SYSTEM AND METHOD TO PROMOTE HEALTHY BEHAVIORS

(75) Inventors: Kelly Murphy-Aniceto, Charlestown, IN (US); Shane Regala, Louisville, KY (US)

(73) Assignee: Humana Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/541,386

(22) Filed: Jul. 3, 2012

Related U.S. Application Data

(63) Continuation of application No. 12/481,325, filed on Jun. 9, 2009, now Pat. No. 8,210,849.

(60) Provisional application No. 61/059,918, filed on Jun. 9, 2008.

(51) Int. Cl.
*G09B 11/00* (2006.01)
*A63F 13/00* (2006.01)

(52) U.S. Cl. .......................... 434/127; 463/1

(58) Field of Classification Search .............. 434/127, 434/322, 323, 350, 365, 267; 463/1, 36
See application file for complete search history.

(56) References Cited

U.S. PATENT DOCUMENTS

| | | | | |
|---|---|---|---|---|
| 2006/0003305 | A1* | 1/2006 | Kelmar | 434/350 |
| 2008/0146334 | A1* | 6/2008 | Kil | 463/36 |
| 2008/0311968 | A1* | 12/2008 | Hunter | 463/1 |

\* cited by examiner

*Primary Examiner* — Kathleen Mosser
(74) *Attorney, Agent, or Firm* — Standley Law Group LLP

(57) ABSTRACT

An online game that promotes healthy behavior by engaging computer users and by providing educational information about health and nutrition. User participation is measured in relation to an avatar of a belly that gains and loses weight according to game play. Users are assigned an avatar according to answers to profile questions. Users earn points by correctly answering health and nutrition questions. When a user answers a question correctly, the player can help him- or herself or "sabotage" a friend. Users also have options to help a friend. The game has consequences for incorrect answers. Updates to a leader board and a message board allow users to see how friends are doing. Social networking aspects of the game keep users engaged and entertained, and therefore, more likely to participate. Participation helps users to increase their knowledge of health and nutrition facts and therefore, their knowledge regarding healthy behaviors.

20 Claims, 30 Drawing Sheets

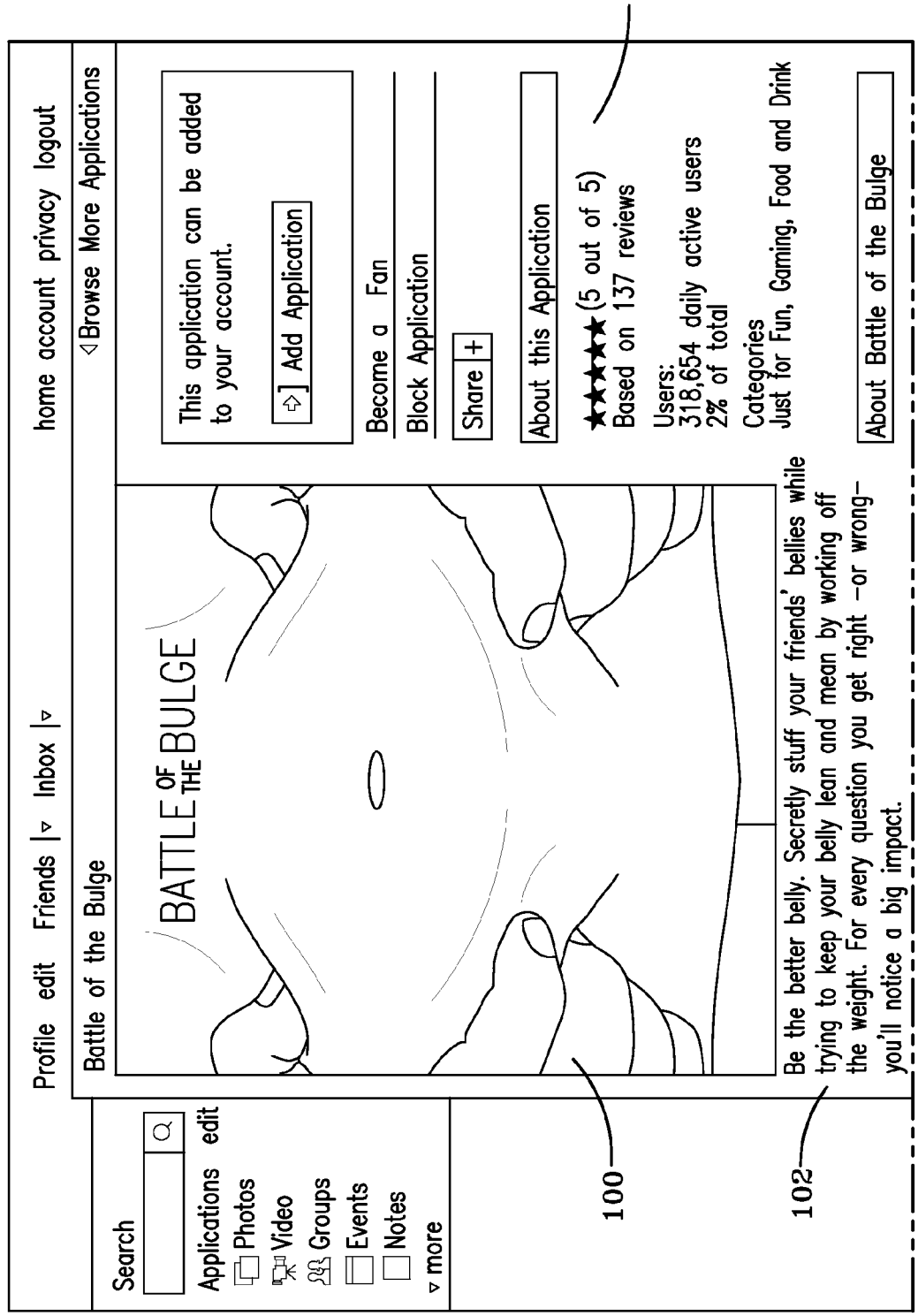

FROM FIG-2A

124

126

How often do you exercise?
◉ Total gym rat
○ 2-3 times a week, maybe
○ Yeah, I might get a Wii Fit—when the Playstation does What's your lifestyle?
◉ I build skyscrapers—with hand tools
○ Chained to the desk 9-5, weekend warrior
○ Dude, I haven't left the couch in three years ☑ Notify your friends

[Continue]  [Cancel]

FIG-2B

FROM FIG-4A

SCORE:

025 DAYS

Time that weight was maintained at 0 lbs.

TOP 75%

Ranked: 155th

This body has been fattened up: 115 TIMES

This body has worked it off: 205 TIMES

144

Carly Jones
aka "Front Butt Buster"

015 DAYS AT 0 | 124TH
CURRENT: 185 LBS

Ken Doe
aka "Chubbs"

See All | Invite

148

Latest Feeds
Displaying 4 stories

See All

👥+1 Ken Doe aka "Chubbs" gave Joe Jones aka "Jabba Da Hut" five pounds to add to his muffin top in the Battle of the Bulge.
1:48pm Add Comment                                                                                      x 👥+1 Joe Jones aka "Jabba Da Hut" sat around doing nothing for a week and gained five pounds in the Battle of the Bulge.
1:48pm Add Comment                                                                                      x

FIG-4B

Profile edit   Friends |▷   Inbox |▷                       home   account   privacy   logout Joe Jones
is working like a dog.
Updated 39 minutes ago   edit Networks:              Kansas City, MO
Sex:                   Male
Relationship Status:   Married
Birthday:              October 31, 1980

Mini-Feed                                                  —158
Displaying 10 stories                        Import | See All Today 👥+1  Ken Doe aka "Chubbs" gave Joe Jones aka "Jabba Da          x
     Hut" five pounds to add to his muffin top in the Battle
     of the Bulge.
     1:48pm Add Comment 🤲   Joe added the Give Refugees a Hand Application 2:39pm      x
     Add Comment 💬   Joe wrote on Ben Dee's wall. 2:37pm                        x ⬜   Joe added the Give Rice Application. 2:36pm               x
     Add Comment Joe is working like a dog. 2:35pm   Add Comment            x 👥+1 Joe and Thomas Z are now friends. 2:34pm                  x
     Add Comment View My Friends (8)

See All
▽ Friends
8 friends

[Andrew    ] [Deb Q    ] [Ben Dee  ]
  [Jones     ]

[Thomas Z  ] [Ken      ] [Carly    ]
              [Doe      ] [Jones    ]

Search  [    🔍]
Applications  edit
☐ Photos
📹 Video
👥 Groups
☐ Events
☐ Notes
☐ Movies
◯ Give Rice
▽ more

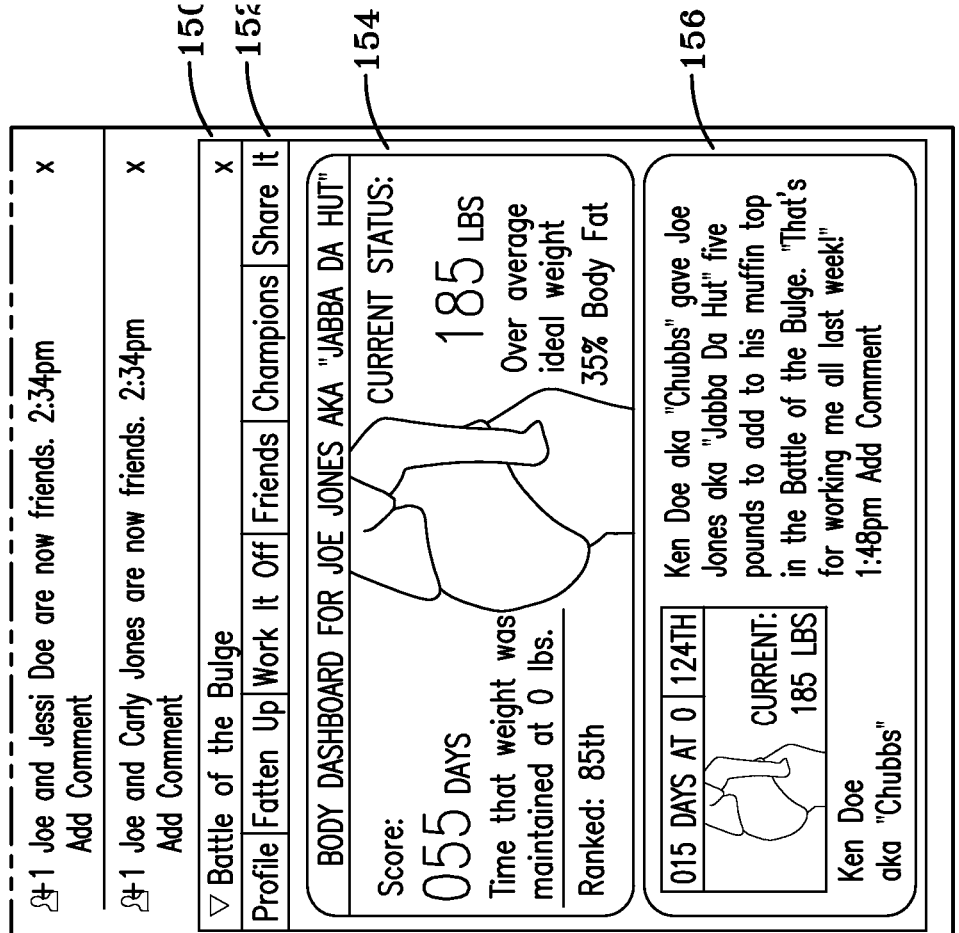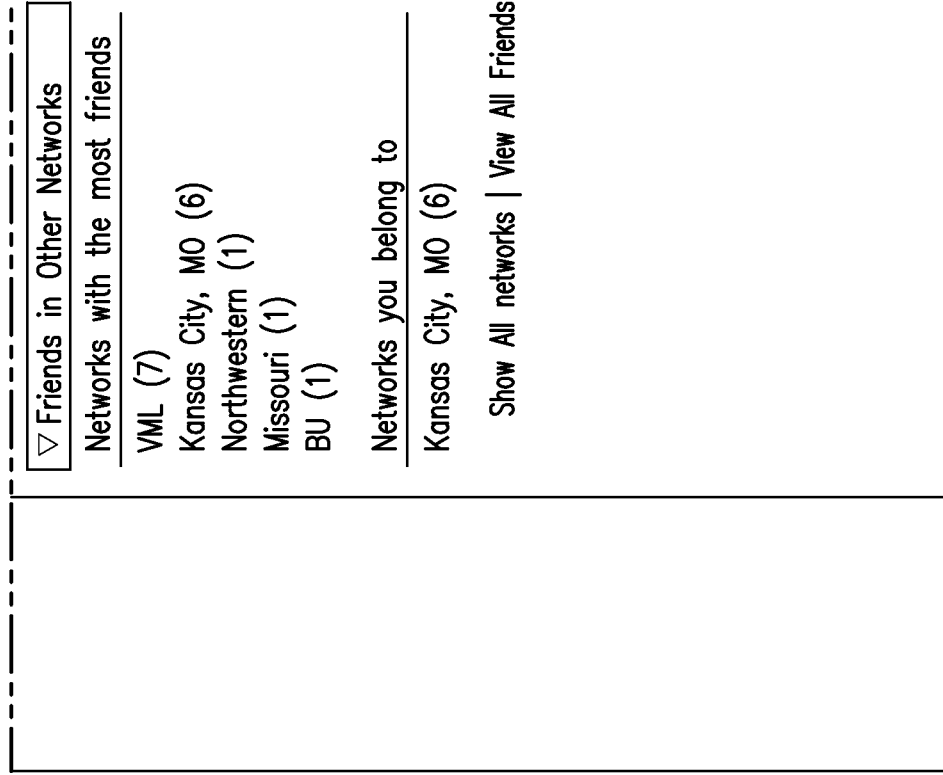
FIG-5B

FROM FIG-6A

| This body has been fattened up: | 115 TIMES | Ken Doe aka "Chubbs" |
|---|---|---|
| This body has worked it off: | 205 TIMES | See All \| Invite |

Latest Feeds — See All

Displaying 4 stories

👤+1  Ken Doe aka "Chubbs" gave Joe Jones aka "Jabba Da Hut" five pounds to add to his muffin top in the Battle of the Bulge.
1:48pm Add Comment    ✗

👤+1  Joe Jones aka "Jabba Da Hut" sat around doing nothing for a week and gained five pounds in the Battle of the Bulge.
1:48pm Add Comment    ✗

👤+1  Jill Brown aka "Mrs. Round" grew Cindy Smith's aka "Yummy Tummy" front butt with five pounds.
1:15pm Add Comment    ✗

👤+1  Rob Doe aka "One Beefy Slim Jim" stuffed Nate Jones aka "Fat Bastard" with five pounds of empty calories.
12:48pm Add Comment    ✗

👤+1  Cindy Smith aka "Yummy Tummy" fed Jill Brown aka "Mrs. Round" five pounds of dead weight.
11:15pm Add Comment    ✗

Figure 7A:
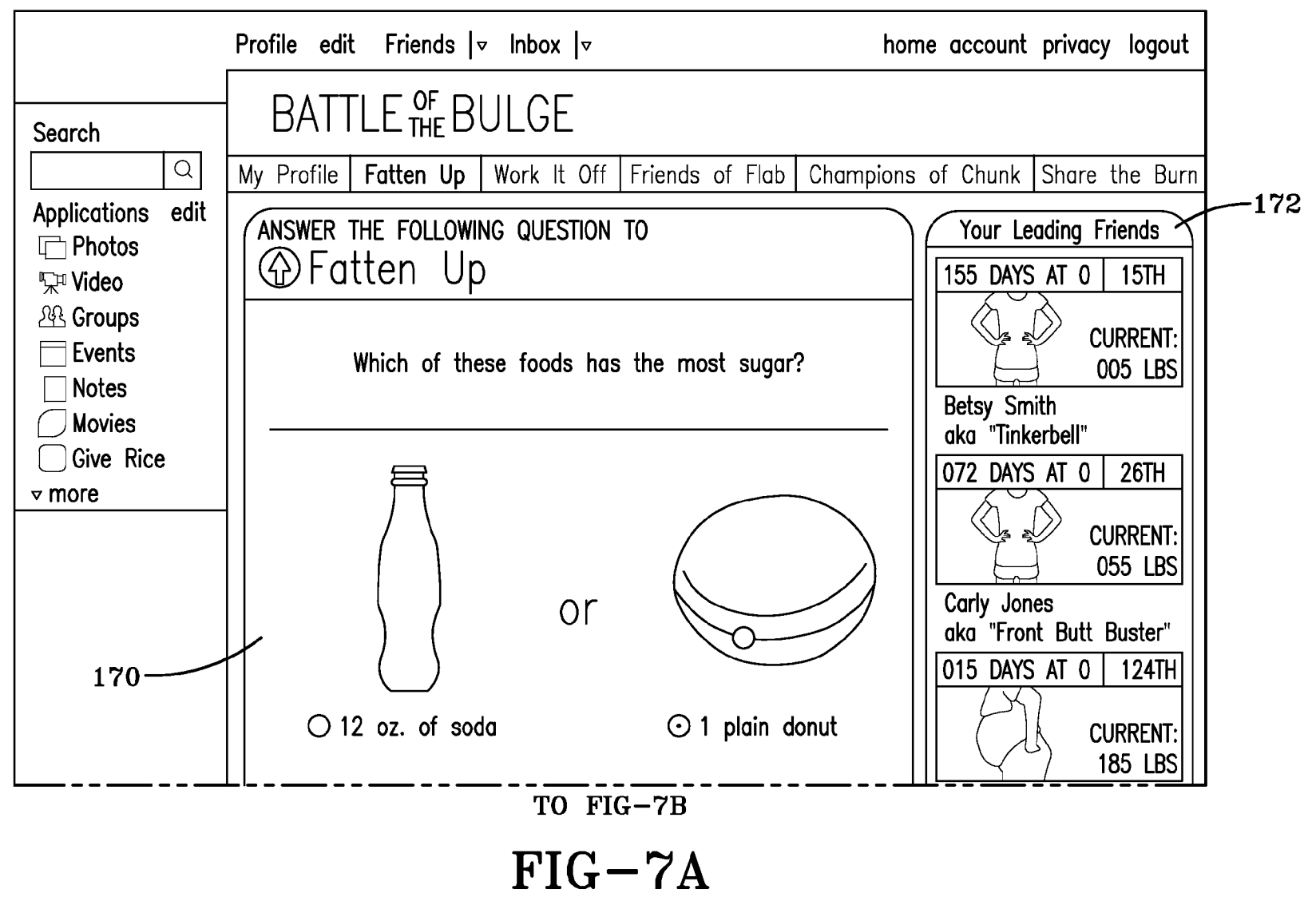

Profile edit  Friends |▽  Inbox |▽                    home account privacy logout

BATTLE OF THE BULGE

| My Profile | Fatten Up | Work It Off | Friends of Flab | Champions of Chunk | Share the Burn |

ANSWER THE FOLLOWING QUESTION TO
⊕ Fatten Up

Which of these foods has the most sugar?

○ 12 oz. of soda    or    ⊙ 1 plain donut

Your Leading Friends — 172

155 DAYS AT 0 | 15TH
CURRENT: 005 LBS
Betsy Smith
aka "Tinkerbell"

072 DAYS AT 0 | 26TH
CURRENT: 055 LBS
Carly Jones
aka "Front Butt Buster"

015 DAYS AT 0 | 124TH
CURRENT: 185 LBS

Search 🔍
Applications edit
☐ Photos
☐ Video
☒ Groups
☐ Events
☐ Notes
☐ Movies
☐ Give Rice
▽ more

FROM FIG-7A

Ken Doe
aka "Chubbs"

Answer

See All | Invite

Latest Feeds See All

Displaying 4 stories

- +1 Ken Doe aka "Chubbs" gave Joe Jones aka "Jabba Da Hut" five pounds to add to his muffin top in the Battle of the Bulge.
  1:48pm Add Comment x

- +1 Joe Jones aka "Jabba Da Hut" sat around doing nothing for a week and gained five pounds in the Battle of the Bulge.
  1:48pm Add Comment x

- +1 Jill Brown aka "Mrs. Round" grew Cindy Smith's aka "Yummy Tummy" front butt with five pounds.
  1:15pm Add Comment x

- +1 Rob Doe aka "One Beefy Slim Jim" stuffed Nate Jones aka "Fat Bastard" with five pounds of empty calories.
  12:48pm Add Comment x

- +1 Cindy Smith aka "Yummy Tummy" fed Jill Brown aka "Mrs. Round" five pounds of dead weight.
  11:15pm Add Comment x

FIG-8A1

FROM FIG-8A1

○ Make me sexy! Drop my own waistline.
⊙ Help a friend drop some needed dead weight.

Ken Doe
aka "Chubbs"

See All | Invite — 188

[Drop Those Pounds]

Latest Feeds | See All
Displaying 4 stories

👥+1 Ken Doe aka "Chubbs" gave Joe Jones aka "Jabba Da Hut" five pounds to add to his muffin top in the Battle of the Bulge.
1:48pm Add Comment                                                                                      x 👥+1 Joe Jones aka "Jabba Da Hut" sat around doing nothing for a week and gained five pounds in the Battle of the Bulge.
1:48pm Add Comment                                                                                      x 👥+1 Jill Brown aka "Mrs. Round" grew Cindy Smith's aka "Yummy Tummy" front butt with five pounds.
1:15pm Add Comment                                                                                      x 👥+1 Rob Doe aka "One Beefy Slim Jim" stuffed Nate Jones aka "Fat Bastard" with five pounds of empty calories.
12:48pm Add Comment                                                                                     x 👥+1 Cindy Smith aka "Yummy Tummy" fed Jill Brown aka "Mrs. Round" five pounds of dead weight.
11:15pm Add Comment                                                                                     x

FIG-8A2

BATTLE OF THE BULGE

Profile edit | Friends |▷ Inbox |▷     home account privacy logout

My Profile | Fatten Up | Work It Off | Friends of Flab | Champions of Chunk | Share the Burn

CONGRATULATIONS, SMARTYPANTS!

✓ Correct!

190

Call the cops! One plain donut has 34 teaspoons of sugar. A typical soda has 12 teaspoons of sugar. That explains a lot.

192

5 ⬇ LBS

You now have 5 lbs. added to your score. Throw these pounds on a friend and watch them balloon up like a blowfish.

194

Your Leading Friends — 196

| 155 DAYS AT 0 | 15TH |
|---|---|
| | CURRENT: 005 LBS |

Betsy Smith
aka "Tinkerbell"

| 072 DAYS AT 0 | 26TH |
|---|---|
| | CURRENT: 055 LBS |

Carly Jones
aka "Front Butt Buster"

| 015 DAYS AT 0 | 124TH |
|---|---|
| | CURRENT: 185 LBS |

Search 🔍

Applications   edit
- 🖥 Photos
- 📹 Video
- 👥 Groups
- 🗓 Events
- 📝 Notes
- 🎬 Movies
- 🍚 Give Rice ▽ more

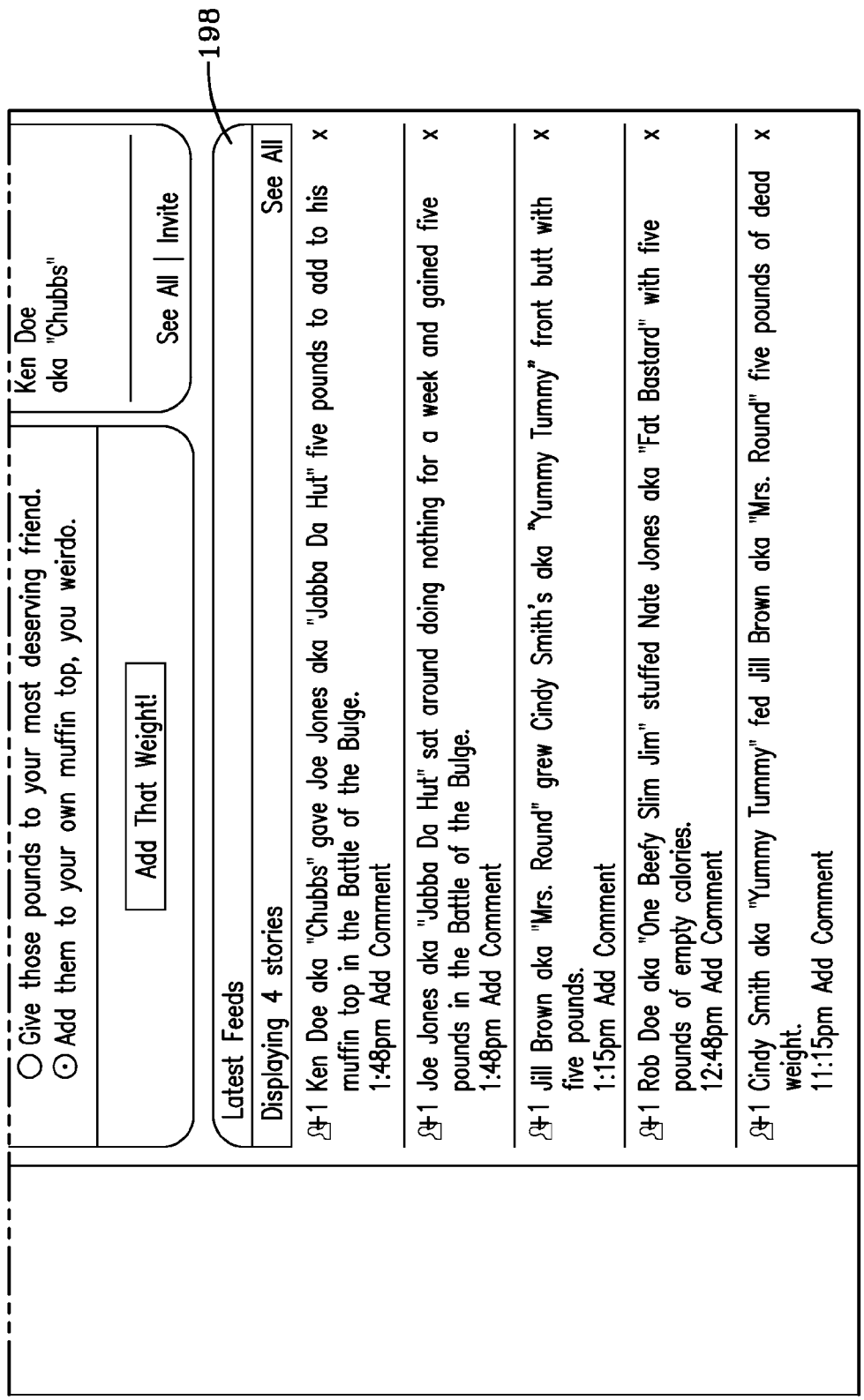
FIG-8B2

FIG-9A

Profile edit  Friends |▽  Inbox |▽                    home account privacy logout

BATTLE OF THE BULGE

| My Profile | Fatten Up | Work It Off | Friends of Flab | Champions of Chunk | Share the Burn |

OOOOH THAT WAS A CLOSE ONE, BUT STILL...
⊗ So Wrong!

200

Call the cops! One plain donut has 34 teaspoons of sugar. A typical soda has 12 teaspoons of sugar. That explains a lot.

202
—1— LBS

Due to your utter lack of ability to properly take care of your body, one point has been added to your profile. Perhaps you should focus on working off your own dead weight.

Search 🔍
Applications  edit
☐ Photos
☐ Video
☐ Groups
☐ Events
☐ Notes
☐ Movies
☐ Give Rice
▽ more

204

Your Leading Friends — 206

155 DAYS AT 0 | 15TH
CURRENT: 005 LBS
Betsy Smith aka "Tinkerbell"

072 DAYS AT 0 | 26TH
CURRENT: 055 LBS
Carly Jones aka "Front Butt Buster"

015 DAYS AT 0 | 124TH
CURRENT: 185 LBS

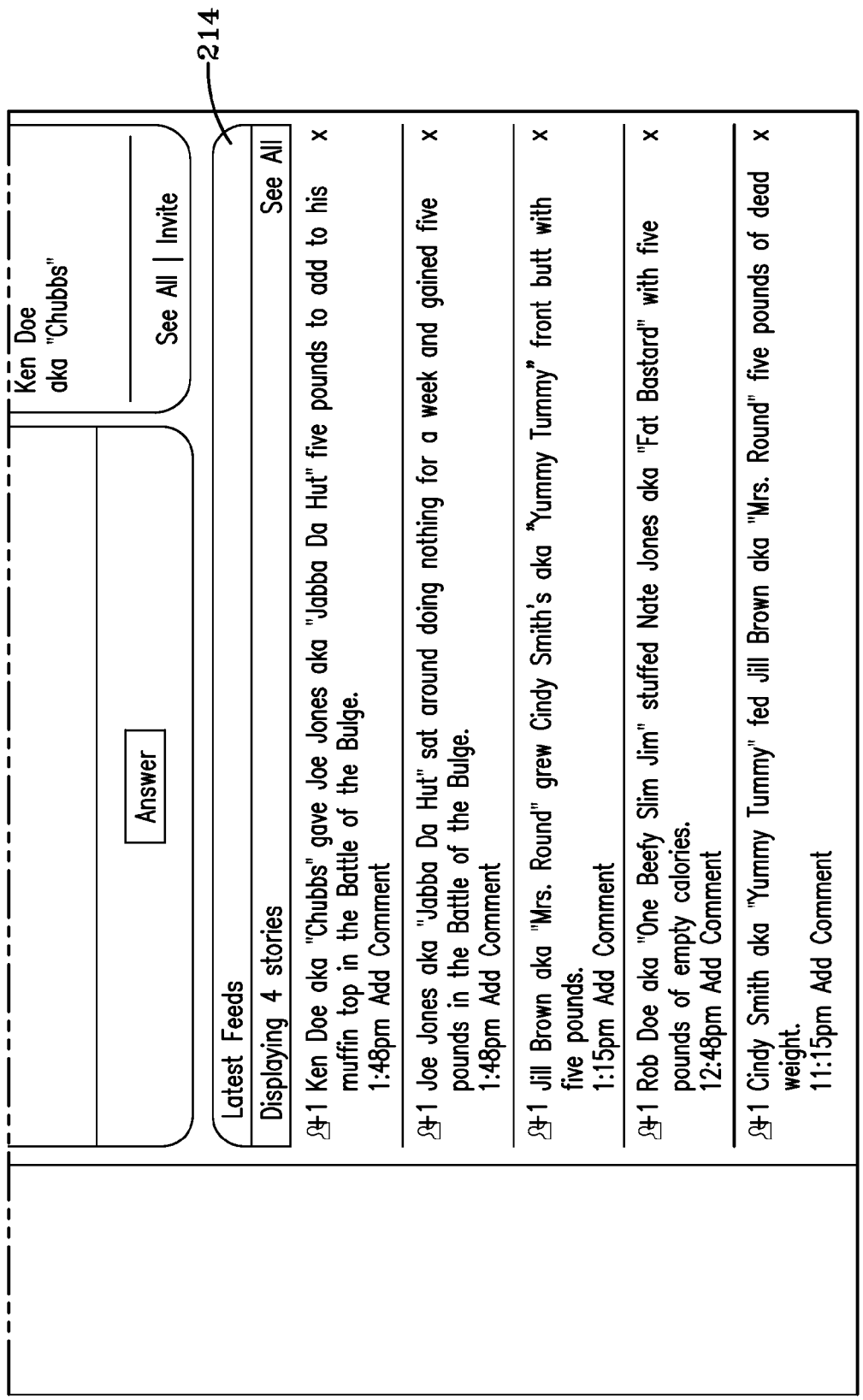
FIG-10A2

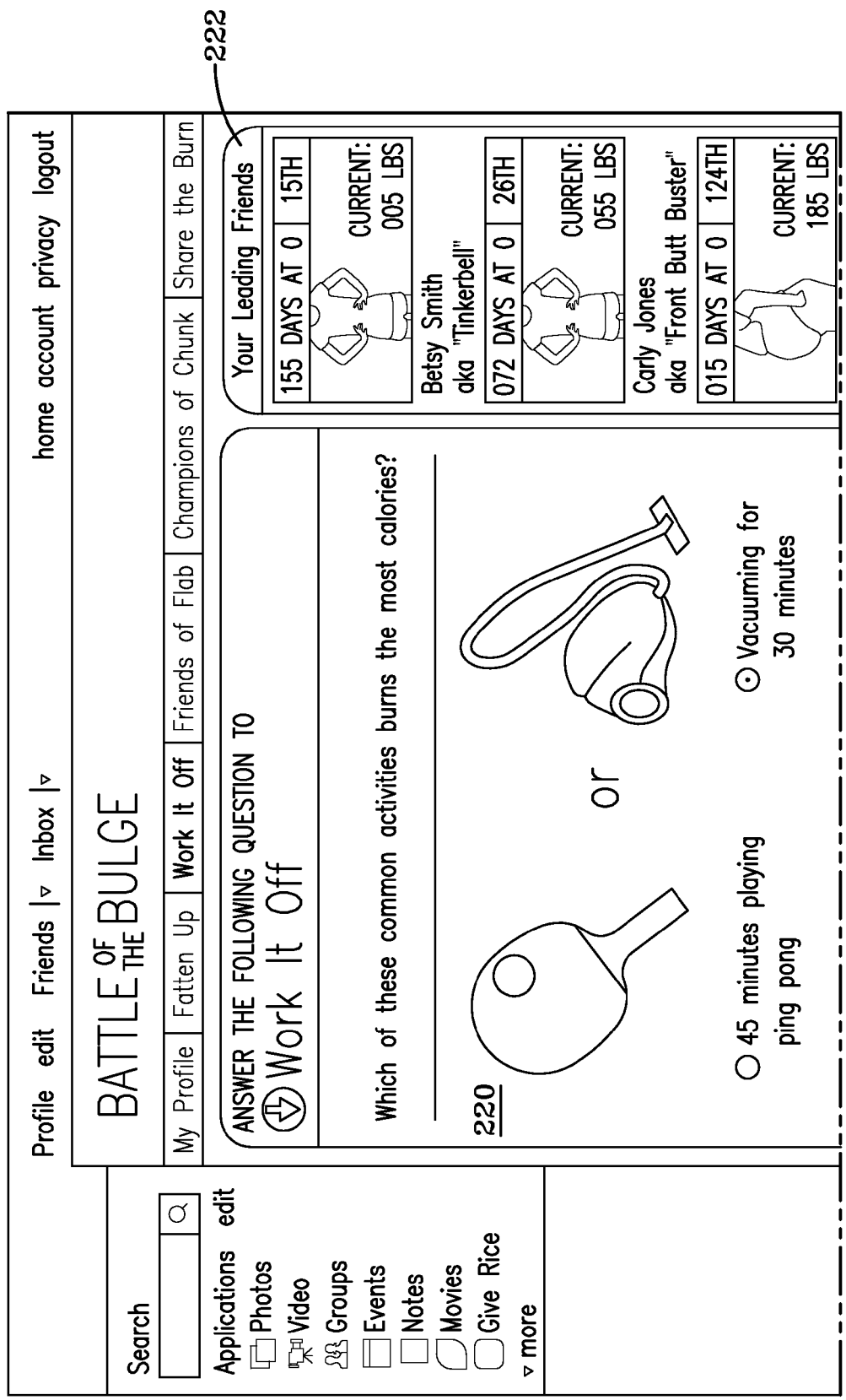
FIG-10B1

FROM FIG-10B1

Answer

Ken Doe
aka "Chubbs"

See All | Invite

— 224

Latest Feeds

Displaying 4 stories                                                    See All

👥1  Ken Doe aka "Chubbs" gave Joe Jones aka "Jabba Da Hut" five pounds to add to his    x
     muffin top in the Battle of the Bulge.
     1:48pm Add Comment 👥1  Joe Jones aka "Jabba Da Hut" sat around doing nothing for a week and gained five    x
     pounds in the Battle of the Bulge.
     1:48pm Add Comment 👥1  Jill Brown aka "Mrs. Round" grew Cindy Smith's aka "Yummy Tummy" front butt with    x
     five pounds.
     1:15pm Add Comment 👥1  Rob Doe aka "One Beefy Slim Jim" stuffed Nate Jones aka "Fat Bastard" with five     x
     pounds of empty calories.
     12:48pm Add Comment 👥1  Cindy Smith aka "Yummy Tummy" fed Jill Brown aka "Mrs. Round" five pounds of dead   x
     weight.
     11:15pm Add Comment

| Search | Profile edit  Friends |▽  Inbox |▽ | home  account  privacy  logout |
|---|---|---|

| Applications edit | BATTLE OF THE BULGE |
|---|---|

| ☐ Photos | My Profile | Fatten Up | Work It Off | Friends of Flab | Champions of Chunk | Share the Burn |
|---|---|---|---|---|---|---|

Behold! The Champions of Chunk

Ranked: 1st

[photo] Andrew Jones aka "Tiny Dancer"

Score: 275 DAYS
Time that weight was maintained at 0 lbs.

CURRENT STATUS:
185 LBS
Over average ideal weight
55% Body Fat

— 250

Ranked: 2nd

[photo] Jessi Doe aka "Thinster"

Score: 212 DAYS
Time that weight was maintained at 0 lbs.

CURRENT STATUS:
045 LBS
Over average ideal weight
35% Body Fat

☐ Video
⚇ Groups
☐ Events
☐ Notes
☐ Movies
☐ Give Rice
▽ more

ONLINE GAME SYSTEM AND METHOD TO PROMOTE HEALTHY BEHAVIORS

CROSS-REFERENCE TO RELATED APPLICATIONS

This application claims priority to U.S. application Ser. No. 12/481,325 filed Jun. 9, 2009, entitled Online Game System and Method to Promote Healthy Behaviors and U.S. Provisional Application Ser. No. 61/059,918 filed Jun. 9, 2008, entitled System and Method for Visualization, Personalization and Mobilization of Health Information, all of which incorporated by reference as if fully recited herein.

FIELD OF THE INVENTION

The present invention relates generally to computerized systems for providing health information to computer users. In particular, the present invention is directed to a computerized system for providing health and nutrition information in the form of an online game that tests individuals' knowledge of health and nutrition.

BACKGROUND OF THE INVENTION

Many web sites on the Internet today have an abundance of health and nutrition information. Although such health and nutrition information is readily available to anyone at the click of a mouse, many people do not seek the information because it is presented in a dry or unengaging manner. When people have free time, they often prefer to use their computers for recreational activities that are more likely to be fun and engaging than educational. Oftentimes, they will use the computer to play games by themselves or with other users of the Internet. Even when people understand the importance of learning about and engaging in healthy behaviors, they will choose activities that are perceived to be fun rather than educational.

One way to make learning about health and nutrition more enticing is to present the information in a way that is more entertaining. One way to make learning health and nutrition information more entertaining is to incorporate it into a game. By incorporating the information into a game, the presentation of information is more interesting than the presentation offered at sites that simply allow individuals to browse information or search directly for it. While a game can make learning more fun, a game that supports multiple players and allows individuals to play against each other is even more engaging and entertaining. Computer users today are particularly attracted to online experiences that allow them to socialize with friends as well as to meet new people to add to their circle of friends. There is a need for an online game that promotes healthy behavior by engaging and entertaining computer users and by providing educational information about health and nutrition to the players. There is a need for an online game that supports social networking while promoting healthy behaviors through education.

SUMMARY OF THE INVENTION

The present invention is an online game that promotes healthy behavior by engaging and entertaining computer users and by providing educational information about health and nutrition to the players. The online game of the present invention supports social networking while promoting healthy behaviors through education. User participation in the game is measured in relation to an avatar of a belly ("belly-tar") that gains and loses weight according to game play. Initially, users are assigned a "belly-tar" according to the answers to a set of profile questions. Users earn points by correctly answering health and nutrition questions. When a user answers a question correctly, the player can help him- or herself or "sabotage" a friend. In other scenarios, a user can help a friend. The game also has consequences for questions that are answered incorrectly. Updates to a leader board and a message board allow users to see how their friends are doing. Social networking aspects of the game help to keep users engaged and entertained, and therefore, more likely to participate. Continued participation helps users to increase their knowledge of health and nutrition facts and therefore, their knowledge regarding healthy behaviors.

BRIEF DESCRIPTION OF THE DRAWINGS

FIGS. 1A and 1B illustrate a sample application home page according to an example embodiment;

FIGS. 2A and 2B illustrate a sample settings page according to an example embodiment;

FIGS. 4A and 4B illustrate a sample welcome page according to an example embodiment;

FIGS. 5A and 5B illustrate a sample profile page for an example embodiment;

FIGS. 6A and 6B illustrate a sample gamer profile page according to an example embodiment;

FIGS. 7A and 7B illustrate a sample "fatten up" question page according to an example embodiment;

FIGS. 8A1, 8A2, 8B1, and 8B2 are sample "fatten up" correct answer pages according to an example embodiment;

FIGS. 9A and 9B illustrate a sample "fatten up" wrong answer page according to an example embodiment;

FIGS. 10A1, 10A2, 10B1, and 10B2 are sample "work it off" pages according to an example embodiment;

FIGS. 11A and 11B illustrate a sample "choose a friend' page according to an example embodiment;

FIGS. 12A and 12B illustrate a sample "friends of flab" page according to an example embodiment;

FIGS. 13A and 13B illustrate a sample "champion of chunks" page for an example embodiment.

DETAILED DESCRIPTION

In an example embodiment of the present invention, the online game for promoting healthy behaviors is implemented as a Facebook™ application. It comprises php files, flash, and other html files that are served from a web site server to a user's computer on request. There is also a database component for storing user and game data. Details of the application and databases are outlined in Appendix A.

FIGS. 1-4 illustrate the flow for adding the application to a user computer.

Step 1. About Application

Figure 1B:
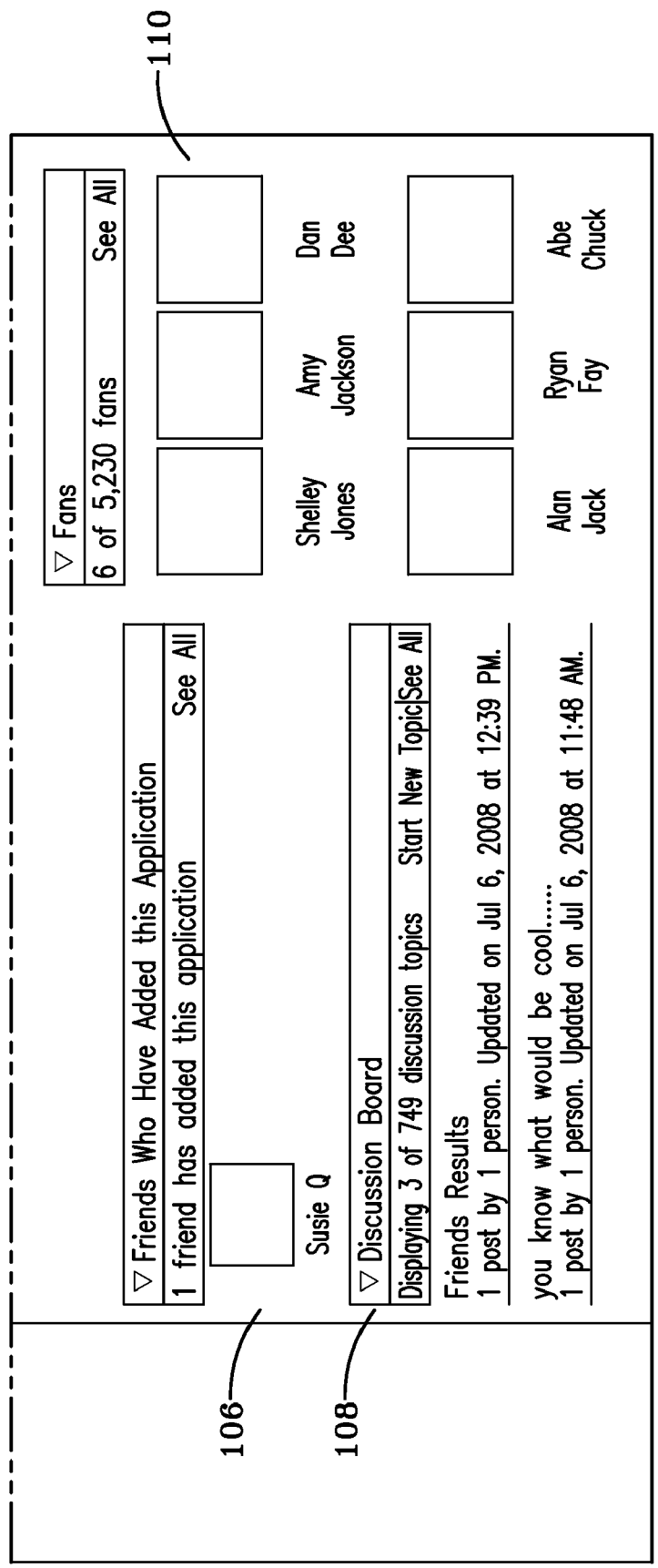

Referring to FIG. 1, a sample application home page according to an example embodiment is shown. The home page elements include an image 100, copy under the image 102, copy for an "about this application" section 104, a "friends who have added this application" section 106, a discussion board 108, and a fans section 110.

Step 2. Add Application

Figure 2A:
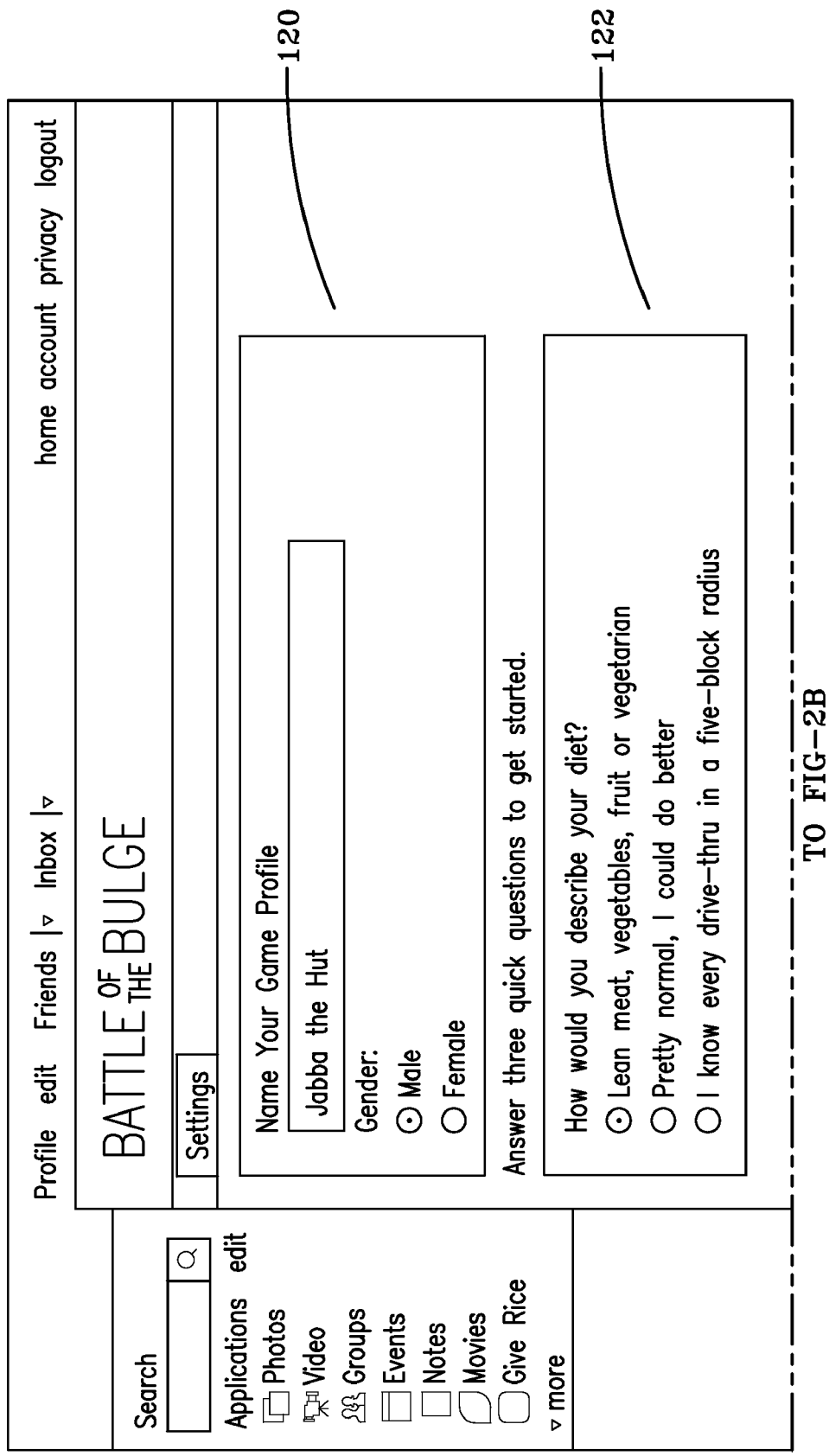

Referring to FIG. 2, a sample settings page according to an example embodiment is shown. The setup elements include a first section with a text box for naming the game profile and gender option (male/female) 120 and a second section with questions and answer options. The question and answer section comprises three multiple choice lifestyle/nutrition questions. The first question 122 relates to the individual's nutrition philosophy. The second question 124 relates to the individual's day-to-day lifestyle. The third question 126 relates to the individual's exercise habits. Points for answers are assigned as follows:

TABLE 1

| Question | Answer | Points |
| --- | --- | --- |
| Nutrition Profile | Lean meat, vegetables, fruit or vegetarian | 0 |
| | Pretty normal, I could do better | 1 |
| | I know every drive-thru in a five block radius | 2 |
| Exercise | Total gym rat | 0 |
| | 2, 3 times a week maybe | 1 |
| | Yeah, I might get a Wii Fit - when the Playstation goes | 2 |
| Lifestyle | I work construction with my hands | 0 |
| | Chained to the desk 9-5 | 1 |
| | Dude, I haven't left the couch in three years | 2 |

Depending on how an individual answers these questions, a "belly" image or avatar of the belly (also called a "belly-tar") is chosen. The selection is based on the gender choice and the number of points accumulated per question. The weight above optimal ranges from 30 pounds to 100 pounds overweight as follows:

TABLE 2

| Points | Pounds over Ideal |
| --- | --- |
| 0 | 30 |
| 1 | 40 |
| 2 | 50 |
| 3 | 60 |
| 4 | 70 |
| 5 | 80 |
| 6 | 100 |

Weights for males range from 200 and 300 pounds for a six foot male (ideal 170) and weights for females range from 170 and 270 pounds for a 5' 9" female (ideal 140). As the game is played, pounds are added to or deducted from each person's avatar so that the physical weight depicted by each user's avatar changes. Each person may view increases or decreases in the physical weight depicted by his or her avatar as the game is played as well as see increases or decreases in the physical weights depicted by other players' avatars.

Step 3. Add Friends

Figure 3:
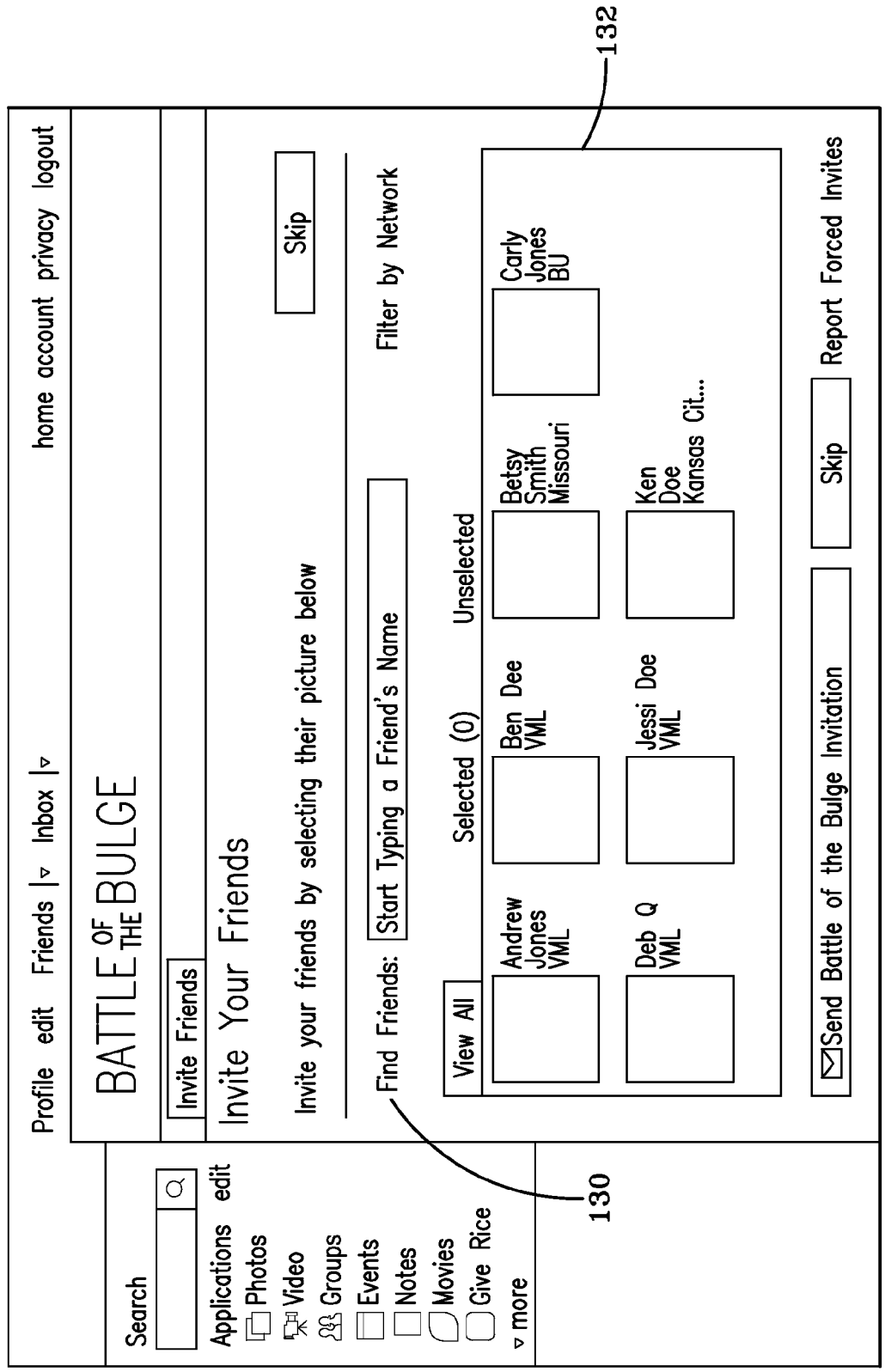
FIG. 3 is a sample add friends page according to an example embodiment.

Referring to FIG. 3, a sample add friends page according to an example embodiment is shown. The user has the option of adding friends by entering their names in a text box 130. Typically, a daily limit is set by the system of between 12-20 friends/per day. The user can select a friend's image to view additional information about the selected friend 132.

Step 4. Welcome Page

Figure 4A:
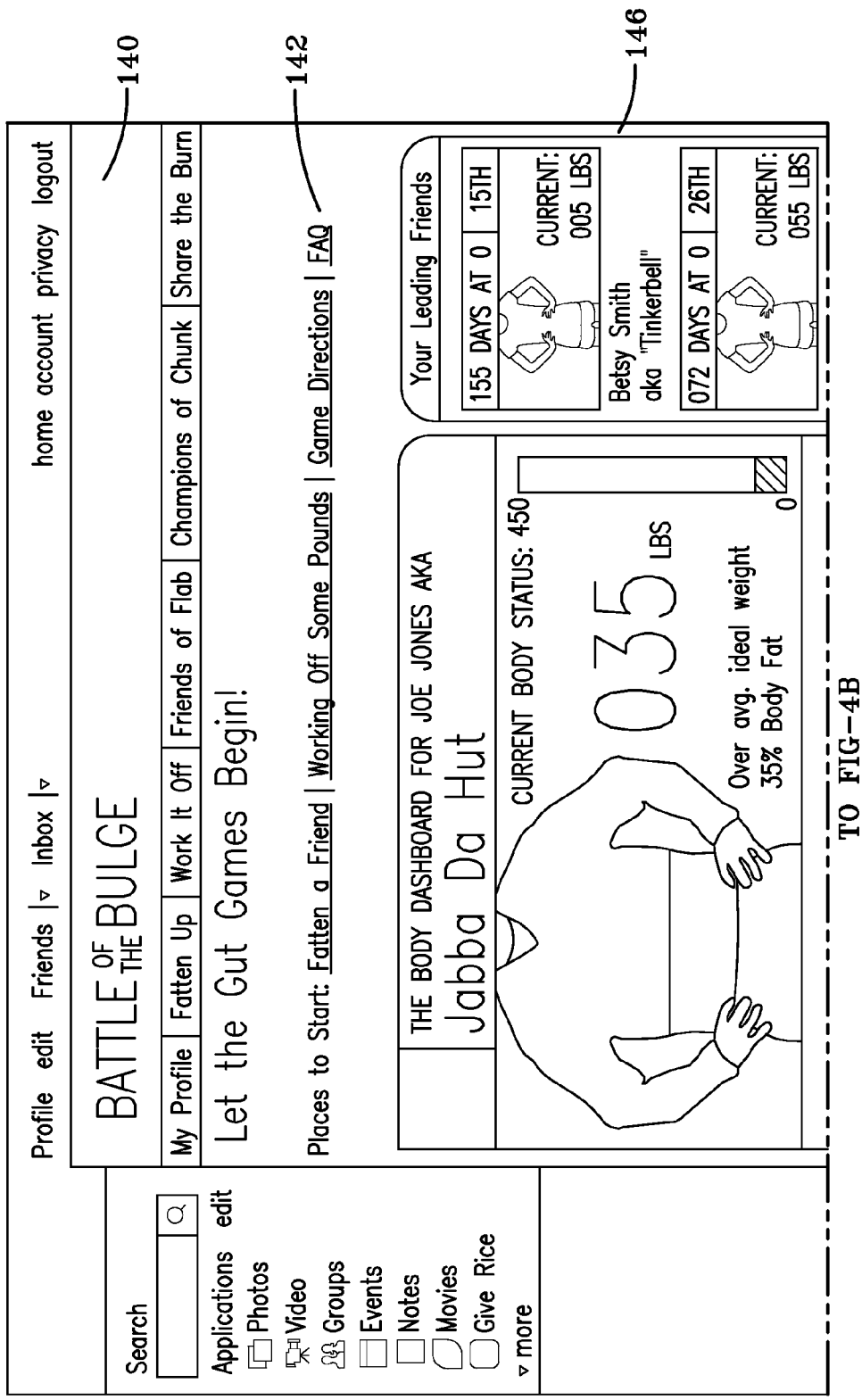

Referring to FIG. 4, a sample welcome page according to an example embodiment is shown. The elements of the page include a welcome message 140, a series of links (Fattening a Friend—link to Fatten Up page; Working Off Some Pounds—link to Work It Off page; Game Directions—link to static game directions; and FAQ—link to static text) 142, a belly avatar or "belly-tar" with an image, name, current number of pounds above ideal weight, percent body fat, a scale of the fat, number of days that have been spent at 0 pounds over ideal, overall game ranking (as a rank against all users), number of times body has gotten fatter, and number of times body has worked it off 144.

Belly images or "belly-tars" may vary as follows:
1. A different image for every 10 pounds over ideal body weight (but less than 100 pounds over);
2. A different image for every 25 pounds above 100 over ideal (but less than 200 pounds over); and
3. A different image for every 50 pounds above 200 but less than 450.

The welcome page further comprises a leader board of friends section 146. In this section, the application may display, for example, results for up to three friends. The results may include the friend's picture, the friend's "belly-tar", and the name of the friend's "belly-tar" as well as current number of pounds above ideal weight and number of days at 0 pounds above ideal weight. A message board appears in a lower portion of the page 148 and displays messages related to the game play.

FIGS. 5-13 illustrate the flow for Playing the Game.

Step 1. Profile Page

Referring to FIG. 5, a sample profile page for an example embodiment is shown. The elements of the page include an application title 150, a link to add the application the user's computer, and links 152 to a profile details page, a "fatten up" page, a "work it off" page, a friends' ("friends of flab") page, a leader board ("champions of chunk") page, and share it ("share the burn") page. The page further comprises a background image and the user's "belly-tar" and belly name. It also shows the user's current weight and number of days at the ideal weight as determined through game play 154. The page further shows the computer user current details for a friend, selected at random from those who have the application, including the number of days the friend has been at 0 pounds over ideal, the friend's image, the friend's "belly-tar" image, the friend's current weight as determined through game play, the friend's name, and the last change in status 156.

Another section of the page displays feed messages such as "Steve took Joe to an all-you-can-eat buffet and he gained 5 lbs. Back at you sucka!" 158. A random food or lifestyle item is added as part of the message (e.g., "ate a box of donuts," "stayed home all week watching the Gilligan's Island Marathon," etc.) The goal of these messages is to provide a level of ongoing engagement and entertainment. Feeds are an important mechanism whereby other social networking members become aware of new applications. Up to 20 unique phrases may be appended to a feed when the user gains weight and 20 unique phrases to use when the user loses weight.

Step 2A. My Profile

Figure 6A:
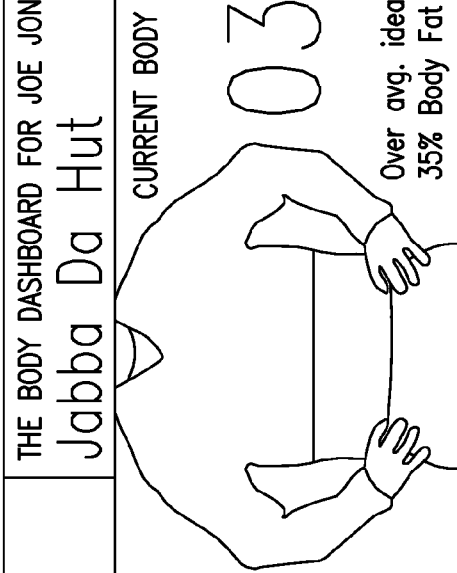

Referring to FIG. 6, a sample gamer profile page according to an example embodiment is shown. The elements of the page include the user's "belly-tar" image and name, current number of pounds above ideal weight, percent body fat, a scale to illustrate the fat, the number of days that have been spent at 0 pounds over ideal, the user's overall game ranking in relation to all users, the number of time the user's "belly-tar" has gained weight and the number of times the user's "belly-tar" has worked off weight 160.

The belly image varies as follows:
1. A different image for every 10 pounds over ideal body weight (but less than 100 pounds over);
2. A different image for every 25 pounds above 100 over ideal (but less than 200 pounds over); and 3. A different image for every 50 pounds above 200 but less than 450.

The page further comprises a leader board of friends displaying each friend's image, "belly-tar" image, and "belly-tar" name as well as current weight over ideal 162. In another section of the page, a message board is displayed 164.

Step 2B. Fatten Up

Referring to FIG. 7, a sample "fatten up" question page according to an example embodiment is shown. This page allows a user to participate in the game by answering health and nutrition related questions. Correct and incorrect answers may have an effect on the user's "belly-tar" weight as well as the "belly-tar" weight of his or her friends.

Which users' weights are affected during game play is determined in part by aspects of the game outside the control of the users and in part by aspects of the game within the users' control as indicated in choices made by the users. In some instances, one user can "sabotage" another user by selecting an option to add pounds to another user's "belly-tar". A user is given the option to "sabotage" another player by answering a health or nutrition answer correctly. In other instances, one user can help another user by selecting an option to remove pounds from another user's "belly-tar". The option to help other players is also presented in connection with correctly answering a health or nutrition question. In this regard, the weight gain and loss scenarios of the game reflect real life scenarios in which factors seemingly out of control of the individual affect the individual's weight loss or gain. Limits on the ability of users to affect each other's weights may be imposed so that one player does not dominate all other players in a group.

In one aspect of the game, a weight maximum may be set for all users such that they do not gain any weight beyond the maximum. The maximum weight parameter (e.g., 450 lbs) may serve to keep certain users in the game that might otherwise have game weights that far exceed other users and as a result, discourage the users from continuing to play the game.

In an example embodiment, one section of the page comprises a multiple choice question relating to a health or nutrition fact 170. For example, the user may be asked to select the food that has the most sugar: 12 oz. soda or 1 plain donut. If the user answers the question correctly, he or she is given an option regarding the game play. For example, the user may have the following options:

1. A: add five pounds to his or her "belly-tar"; or
2. B: add five pounds to a friend's "belly-tar"

If the person is at a maximum weight (e.g., 450 lbs), then the user may be presented with one option of adding five pounds to a friend's "belly-tar." If the question is answered incorrectly, then the weight of the user's "belly-tar" is adjusted. For example, one pound may be added to the user's "belly-tar." The user is then presented with the option of answering another question. If the user is already at the maximum weight, no further weight is added. A limit for questions may be established such that a user is permitted once per day to correctly answer one question and apply pounds against each friend that has the application installed. The page may further comprise a section with a leader board of friends 172. As changes in weight are recorded, comments are added to the message board 174.

Referring to FIGS. 8A and 8B, sample "fatten up" correct answer pages according to an example embodiment are shown. Each page comprises an answer detail section 180, 190 that provides additional health or nutrition information related to the "fatten up" question, a game result section indicating a change in the user's score as a result of answering the question correctly 182, 192 and a game play option section 184, 194 allowing the user to make a selection regarding use of the points awarded for answering the question correctly. The user has the option of reducing his or her own "belly-tar" weight or adding weight to the "belly-tar" of a friend. Selection of the "drop those pounds" option 184, 194 completes the game play. The page further comprises a leader board section 186, 196 and message section 188, 198.

Figure 9B:
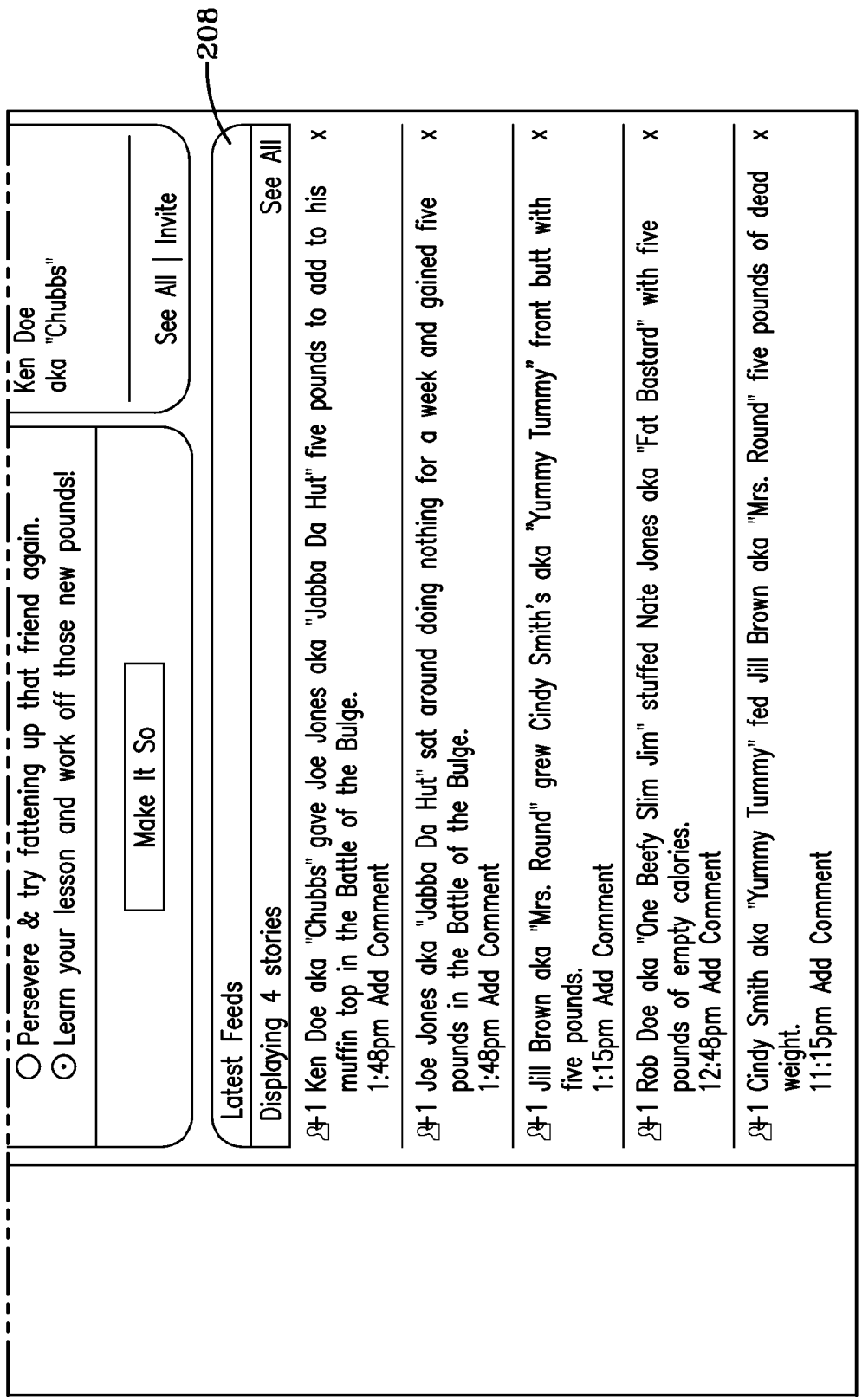

Referring to FIG. 9, a sample "fatten up" wrong answer page according to an example embodiment is shown. The wrong answer page comprises an answer detail section 200 that provides additional health or nutrition information related to the question, a game result section indicating the change in the user's score as a result of answering the question incorrectly 202, and a game play option section 204 allowing the user to make a selection related to continued play of the game. The user has the option of answering another question or proceeding to a "work it off" page. The page further comprises a leader board section 206 and message board section 208.

Step 2C. Work It Off "Belly-Tar"

Figure 10A1:
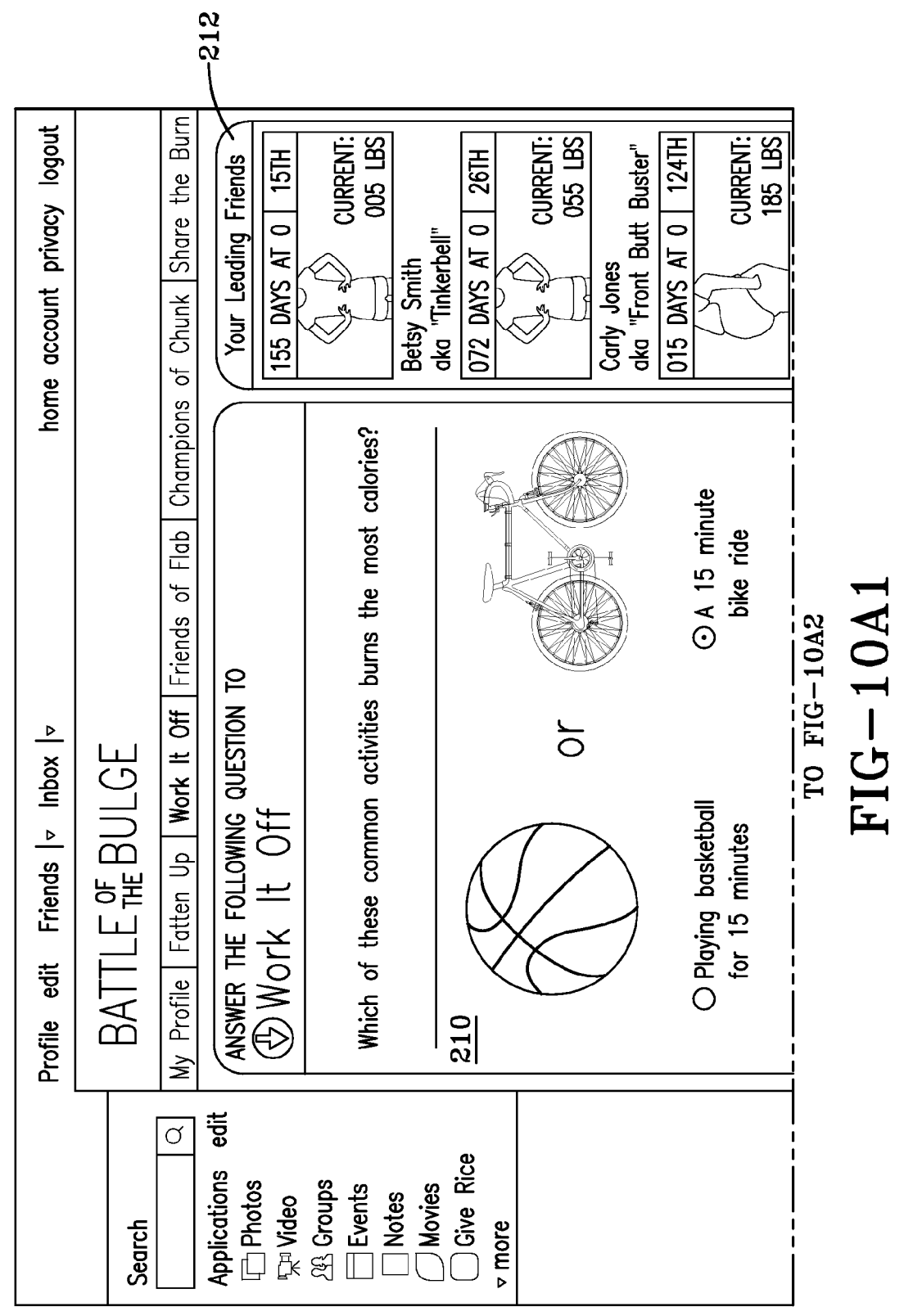

Referring to FIGS. 10A and 10B, sample "work it off" pages according to an example embodiment are shown. A "work it off" page comprises a first section with a multiple choice question regarding a healthy activity 210, 220 and answer option. It further comprises a leader board section 212, 222 and message board section 214, 224.

Step 2C. Work It Off Correct Answer

Upon answering the "work it off" question correctly, the user has the option of removing five pounds from his or her "belly-tar" or taking five pounds off a friend's "belly-tar" as illustrated in FIGS. 8A and 8B. If the person is at the ideal target weight, then the user has the option of taking five pounds off of a friend's "belly-tar". If the question is answered incorrectly, then another question is presented to the user. If the user misses five questions a row, he or she is locked out from this area of the site for 24 hours. As the user's weight changes in relation to pounds that are added or removed, updates to the message board are posted for other players to view. The number of questions that a user is permitted to answer each day may be limited, for example, to five.

Step 2C. Choose a Friend

Figure 11A:
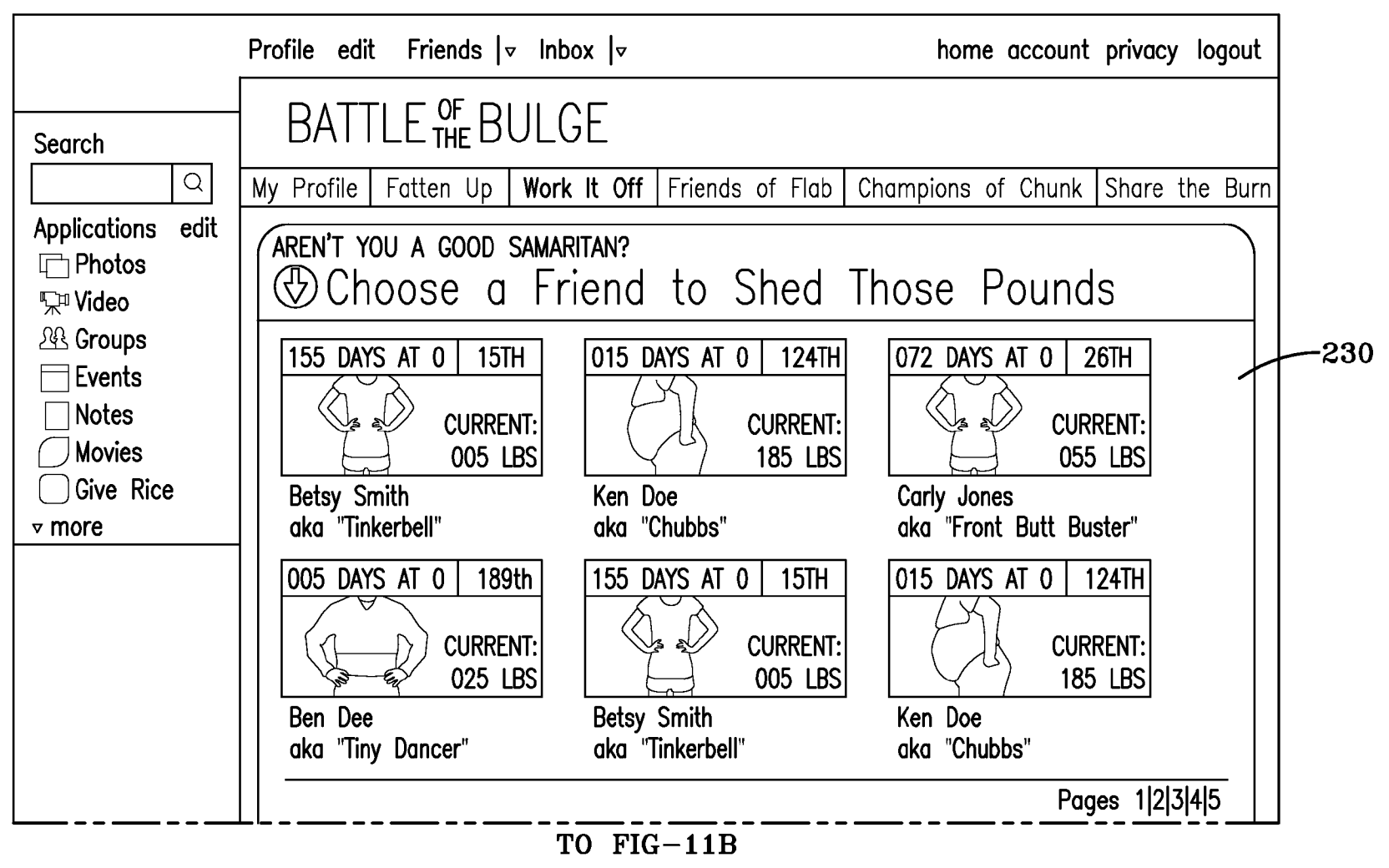
Figure 11B:
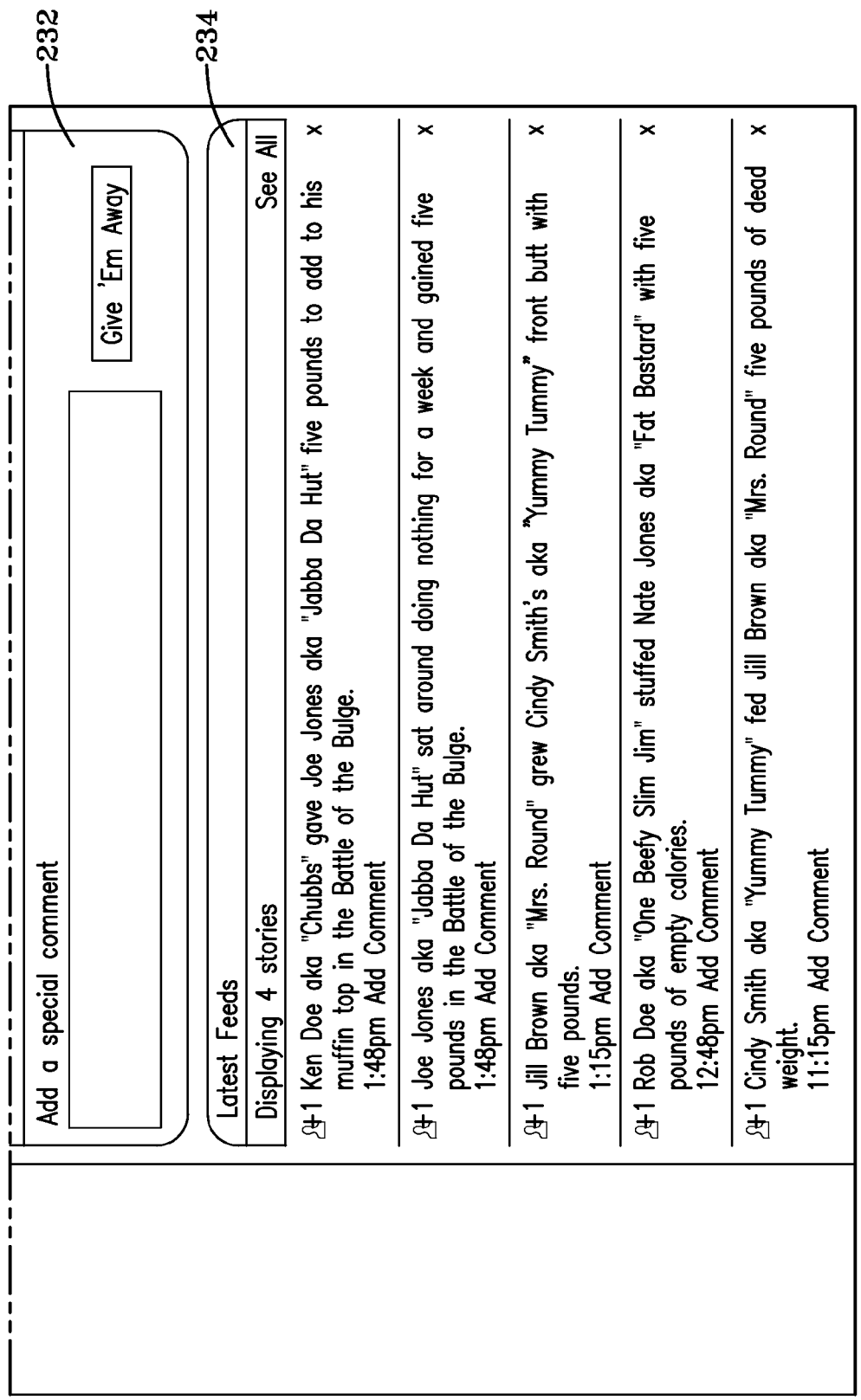

Referring to FIG. 11, a sample "choose a friend' page according to an example embodiment is shown. Identifying and status information for a plurality of the user's friends is displayed 230. The user may browse multiple pages of information for his or her friends before selecting a friend to receive the pounds. The user selects a friend and then selects a "give 'em away" option 232. The user may also enter a comment 232. Finally, a message board appears on the page 234.

Step 2D. Friends of Flab

Figure 12A:
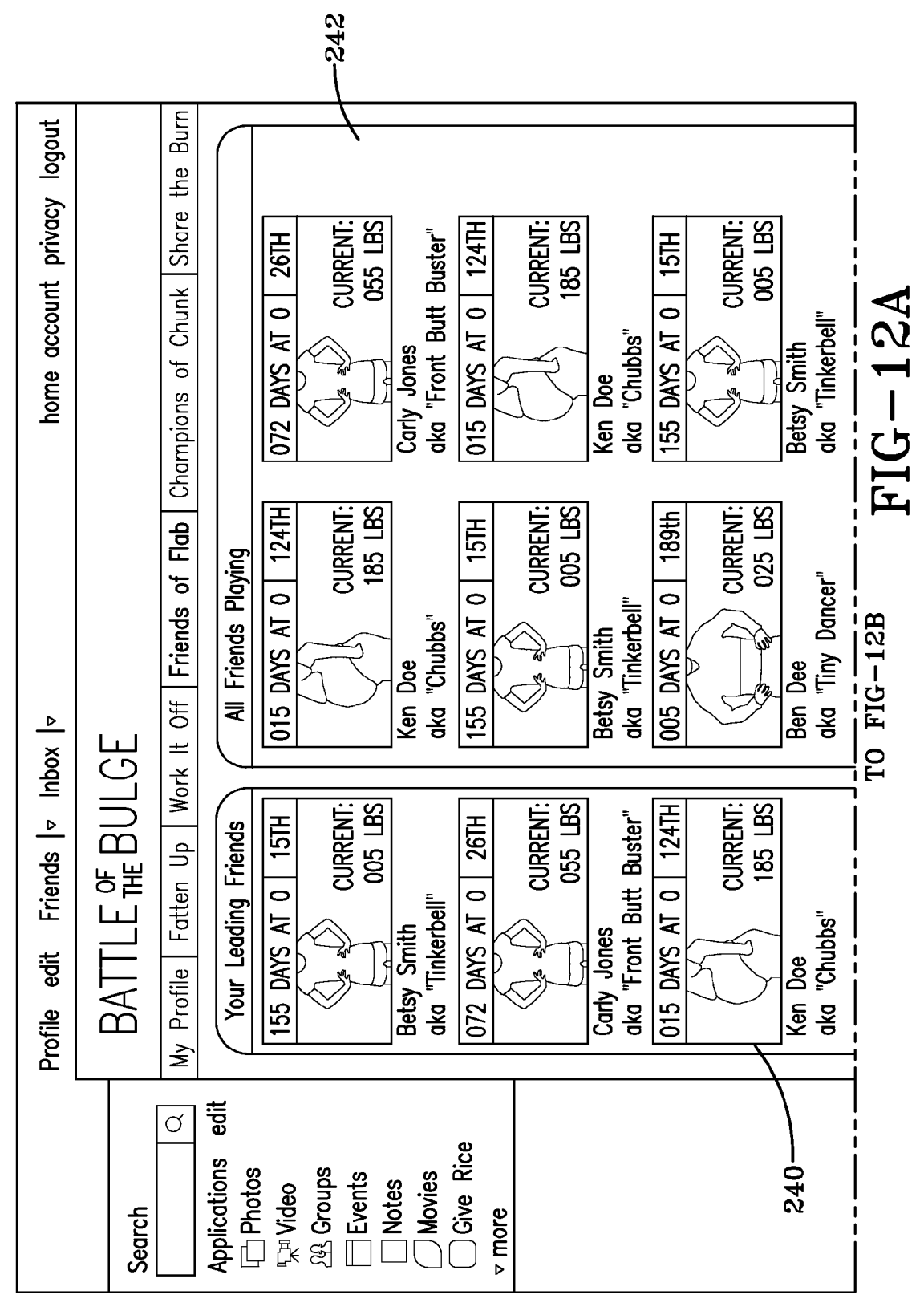
Figure 12B:
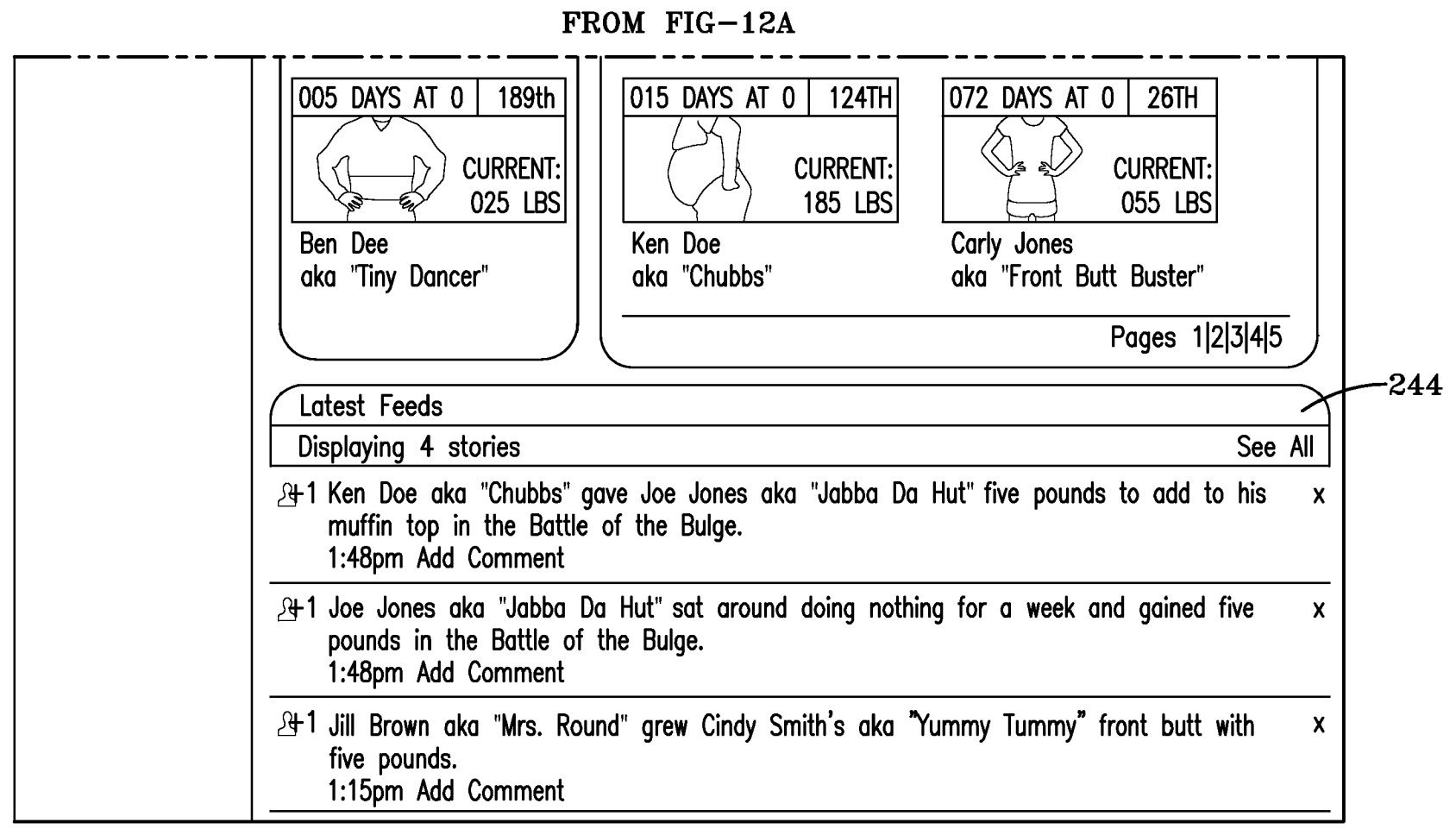

Referring to FIG. 12, a sample "friends of flab" page according to an example embodiment is shown. A first portion of the page has a leader board identifying a plurality of friends (e.g., four) 240. A second portion of the page provides an alphabetical listing of the user's friends that have the application 242. The user can browse the listing and see current information for all of his or her friends. Finally, a message board appears on the page 244.

Figure 13B:

Referring to FIG. 13, a sample "champion of chunks" page for an example embodiment is shown. The page displays a listing of players 250 with the highest weights over ideals. The user with the largest number of pounds over average ideal weight is listed first.

Other rules of the game may be designed to engage users who have been inactive for a period of time. For example, every night, application users who have been inactive over the last 24 hour period (defined as neither "fattening up" nor "working it off") may be targeted for a random event. A portion of inactive users (e.g., 20%) may be identified in an event involving an entry for the message board such as "Wendy went on a pizza binge and ate the whole pizza" and the addition of five pounds to the user's "belly-tar." Twenty such unique descriptions may be developed and randomly assigned to inactive users. The random messages add some light humor to the game and are designed to engage users who have previously expressed an interest in the game but have not participated recently. Random messages that are targeted to inactive users may spur the users to resume their participation in the game.

Figure 14:
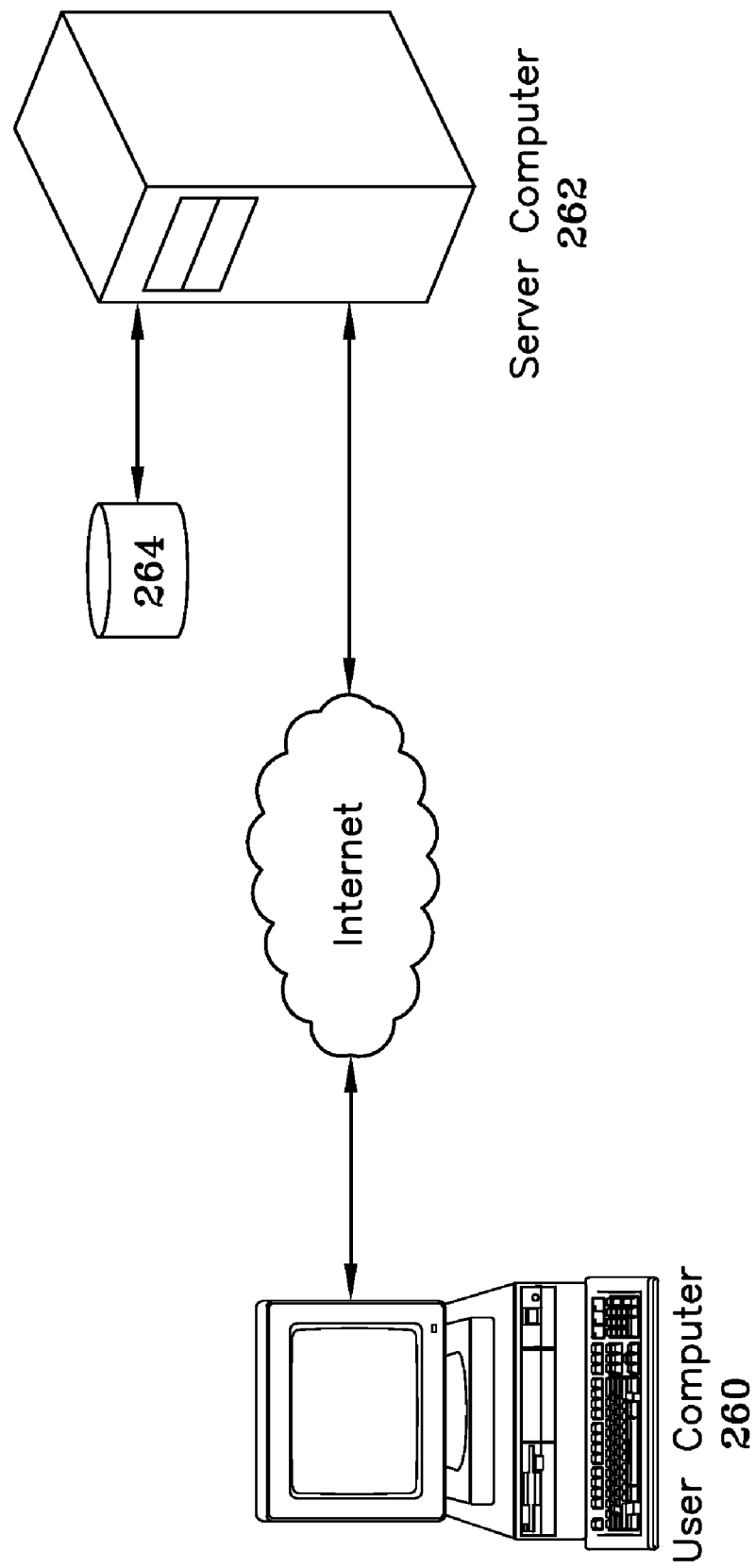
FIG. 14 is a block diagram of hardware components to support user interaction with a web site according to an example embodiment.

Referring to FIG. 14, a block diagram of hardware components to support user interaction with a web site according to an example embodiment is shown. A user computer 260 connects via the internet to a server computer 262. The server computer 262 has software components that create and deliver web pages to the user computer 260 comprising content as described above. Data for questions and answers, message data, and user data for individuals may be stored in the database 262. Data related to groups of computer users that identify each other as friends is also stored in the databases 262. Server software supports the registration and online profile activities. The software further supports the game play and tracking of points and weights for individual players. The software also supports user selections of answers to as well as selections of friends to help or sabotage during game play.

The present invention promotes healthy behavior by presenting health and nutrition information in an entertaining way. Social networking aspects of the invention allow individuals to have an engaging experience. As the game is played, friends are provided with options to help each other and to "sabotage" each other. These aspects of the game reflect real-life scenarios in which individuals who are working diligently toward improving their health may be sidetracked from time-to-time by seemingly uncontrollable events. Friends can also track each other's status through a leader board or by periodically reviewing how their friends are doing. Finally, the message board adds elements of humor to the game to keep individuals entertained and engaged.

While certain embodiments of the present invention are described in detail above, the scope of the invention is not to be considered limited by such disclosure, and modifications are possible without departing from the spirit of the invention as evidenced by the claims. For example, point values for questions and options associated with game play may be modified and fall within the scope of the claimed invention. One skilled in the art would recognize that such modifications are possible without departing from the scope of the claimed invention.

APPENDIX A

Implementation Details

1) Create a uniquely named development application for testing. If necessary, detailed instructions can be found here: http://wiki.developers.facebook.com/index.php/Creating_Your_First_Application
2) Mark application as private in the Developer Application by selecting Edit Settings →Advanced→Enable Sandbox Mode→enable (Checkbox).
3) Create a development environment to mirror the production environment. For example: development.hostdomain.com/battleofthebulge
4) Create a case entry for development application in config.php following the example of existing cases.
5) Copy the API Key and Secret from Application→Edit Settings→Basic, under Essential Information, replace corresponding values.
6) Remove existing entries for VML domains.
7) Set Callback URL to the document root of development installation in the Developer Application→Edit Settings→Basic→Basic Information→Callback URL
8) Set Canvas URL to the name chosen in step 1 (lowercase, alpha, no spaces) in the Developer Application→Edit Settings→Canvas→Canvas URLs→Canvas Page URL
9) Repeat steps for production environment.
10) Deploy and test development application. Once thoroughly tested, deploy to the production server.
11) Once the production application has been tested, change the Callback URL from its current value to the location of a stage environment.
12) Change the Callback URL of Battle Of The Bulge to the value replaced in step 11.
13) Test. If anything appears to be wrong, change the Callback URL to its former value until the problem is resolved.
14) Repeat 12-13 until everything is working.

About the Database

The database is implemented as a small set of tables. A few are related, most contain manually entered, static copy.

Tables activities—contains copy used to build Work It Off questions and answers.

bob_user—contains user data.

failed_feed_stories—used to store a reference to a weight transaction row, in the event that an attempt to publish a feed to the user's wall generates an error or loss of session occurs, due to the "stateful" nature of Flash movies.

feed_copy—static table containing copy used to build feeds from templates foods—a static table containing names, image filenames and four fields containing copy used to build Fatten Up questions and answers for the different foods being compared.

food_items_view—a view of a join between foods, high_low_nutrients, food_nutrients food_nutrients—detail table of foods, containing a field for each nutrient to be evaluated and a common 'food_id' field to associate it with a food, where the value is an amount and the data type for each is decimal. Also contains a 'serving' field for convenience of noting a serving size other than "per serving".

high_low_nutrients—detail table of foods, containing a field for each nutrient to be evaluated and a common food_id to associate it with a food, where the data type for each is enum ('H', 'L').

inactivity_penalties—currently, this table is standing by to store values produced by inactivity_cron.php.

request_log—utility table mostly used for logging errors that do not produce actual HTTP errors.

weight_transactions—used to store information about user interactions.

Files auth auth_callback.php—this script is pinged with a "fb_sig_user" once a user has authorized an application removed.php—this script is pinged with a "fb_sig_user" when a user removes the application includes css.php—included, as linked stylesheets feeds.php—"Fake" feeds generated for application only
header.php—includes lib.php (which includes other files needed for visible pages)
leading_friends.php—included in friends.php
lib.php—global functions, including profile creation and updating
playing_friends.php—playing_friends.php
settings_form.php—filled out by user on first load and after "death", or removal
welcome.php—included just below the header on the first day a user adds the app js
swfobject.js—utility for embedding flash movies when app is within iframe (IE6) util
BOBCalculator.php—simple formulas to determine weight group and BFP
DBUtil.php—basic connection, truncate, clean user input functions
paginator.php—pagination of champs, friends
vo—simple value objects
Question and Answer classes overload_toString( ) to print xml description BOBAnswer.php
BOBQuestion.php—base class for FattenUpQuestion and WorkItOffQuestion classes
BOBUser.php—represents a row in the bob_user table+some convenience variables
FacebookUser.php—Base class for user classes
FattenUpQuestion.php
WorkItOffQuestion.php
Global Navigation
champs.php—the leader board
directions.php—How to play.
faq.php—Frequently Asked Questions—about the game.
fatten_up.php—the Fatten Up quiz container
friends.php—Friends of Flab tab. Includes both playing_friends.php and leading_friends.php
index.php—varies based on the state of user, default is dashboard.
invite.php—friend selector used to invite friends to play.
work_it_off.php—the Work It Off quiz container
Quiz/Flash Movies
Dashboard.swf—view of user stats
FattenUp.swf—the Fatten Up quiz client.
quiz relay.php—instantiates a QuizService instance and passes request parameters for asynch communication.
QuizService.php—class responsible for generating quiz questions and answers. The answers are in sets of 2, one is flagged as being correct
relay.php—instantiates a BOBService instance and passes request parameters for asynch communication. Handles much of the logic for responding/processing results to a quiz, as well as channeling requests for user stats.
WorkltOff.swf—the Work It Off quiz client
Other
days_at_zero_cron.php—this is the primary basis for rankings and should be set to run at midnight (timezone where the application server lives).
inactivity_cron.php this is a cron task to "punish" users for not playing by adding weight at random.
fattenup.php—manually loaded into an iframe, rather than than using fb:swf (IE6)
workitoff.php—manually loaded into an iframe, rather than than using fb:swf (IE6) expressinstall.swf—utility used to assist upgrade of flashplayer.

What is claimed is:

1. A computer implemented online game to promote healthy behaviors, comprising the steps of:
   (a) assigning at a server to each of a plurality of computer users an avatar for use during game play, said avatar assigned to each user according to a score calculated for said user based on said user's answers to a plurality of personal health questions;
   (b) facilitating online game play at said server by:
      (1) presenting said avatars for display at said users' computers;
      (2) prompting said users for answers to health knowledge questions;
      (3) modifying the appearance of said avatars according to said users' answers to said health knowledge questions; and
      (4) presenting said modified avatars for display at said users' computers.

2. The computer implemented online game of claim 1 wherein (b)(2) modifying the appearance of said avatars comprises decreasing the size of at least one of said avatars in response to receiving a correct answer from a user.

3. The computer implemented online game of claim 1 wherein (b)(2) modifying the appearance of said avatars comprises increasing the size of at least one of said avatars in response to receiving an incorrect answer from a user.

4. The computer implemented online game of claim 1 wherein (b)(2) modifying the appearance of said avatars comprises decreasing the size of at least one of said avatars in response to a request from a user assigned to said avatar providing a correct answer to a health knowledge question.

5. The computer implemented online game of claim 1 wherein (b)(2) modifying the appearance of said avatars comprises increasing the size of at least one of said avatars in response to a request from a user not assigned to said avatar providing a correct answer to a health knowledge question.

6. The computer implemented online game of claim 1 wherein (b)(2) modifying the appearance of said avatars comprises modifying a physical weight depicted by an avatar.

7. The computer implemented online game of claim 1 wherein (b)(2) modifying the appearance of said avatars comprises decreasing a physical weight depicted by an avatar in response to receiving a correct answer to a health knowledge question.

8. The computer implemented online game of claim 1 wherein (b)(2) modifying the appearance of said avatars comprises increasing a physical weight depicted by an avatar in response to receiving an incorrect answer to a health knowledge question.

9. The computer implemented online game of claim 1 wherein said health knowledge questions comprise nutrition questions.

10. A computer implemented online game to promote healthy behaviors, comprising:
    (a) a database storing for each of a plurality of computer users:
       (1) a user identifier; and
       (2) an avatar assigned to said user for use during game play, said avatar assigned to each user according to a score calculated for said user based on said user's answers to a plurality of personal health questions;
    (b) a server executing online game play instructions comprising:
       (1) presenting said avatars for display at said users' computers;
       (2) prompting said users for answers to health knowledge questions;
       (3) modifying the appearance of said avatars according to said users' answers to said health knowledge questions; and (4) presenting said modified avatars for display at said users' computers.

11. The computer implemented online game of claim 10 wherein (b)(3) modifying the appearance of said avatars comprises decreasing the size of at least one of said avatars in response to receiving a correct answer from a user.

12. The computer implemented online game of claim 10 wherein (b)(3) modifying the appearance of said avatars comprises increasing the size of at least one of said avatars in response to receiving an incorrect answer from a user.

13. The computer implemented online game of claim 10 wherein (b)(3) modifying the appearance of said avatars comprises decreasing the size of at least one of said avatars in response to a request from a user assigned to said avatar providing a correct answer to a health knowledge question.

14. The computer implemented online game of claim 10 wherein (b)(3) modifying the appearance of said avatars comprises increasing the size of at least one of said avatars in response to a request from a user not assigned to said avatar providing a correct answer to a health knowledge question.

15. The computer implemented online game of claim 10 wherein (b)(3) modifying the appearance of said avatars comprises modifying a physical weight depicted by an avatar.

16. The computer implemented online game of claim 10 wherein (b)(3) modifying the appearance of said avatars comprises decreasing a physical weight depicted by an avatar in response to receiving a correct answer to a health knowledge question.

17. The computer implemented online game of claim 10 wherein (b)(3) modifying the appearance of said avatars comprises increasing a physical weight depicted by an avatar in response to receiving an incorrect answer to a health knowledge question.

18. The computer implemented online game of claim 10 wherein said health knowledge questions comprise nutrition questions.

19. A computer implemented online game to promote healthy behaviors, comprising the steps of:
   (a) assigning at a server to each of a plurality of computer users an avatar for use during game play, said avatar assigned to each user according to a score calculated for said user based on said user's answers to a plurality of personal health questions;
   (b) facilitating online game play at said server by:
     (1) presenting said avatars for display at said users' computers;
     (2) prompting said users for answers to health knowledge questions;
     (3) receiving from users of correct answers to said health knowledge questions requests to modify appearances of said avatars;
     (4) modifying the appearance of said avatars according to said users' answers to said health knowledge questions; and
     (5) presenting said modified avatars for display at said users' computers.

20. The computer implemented online game of claim 19 wherein said health knowledge questions comprise nutrition questions.

* * * * *